(12) United States Patent
Rhode et al.

(10) Patent No.: US 8,758,706 B2
(45) Date of Patent: Jun. 24, 2014

(54) DEVICE FOR RECEIVING, TREATING, AND STORING SMALL VOLUME SAMPLES

(75) Inventors: Heidrun Rhode, Hainichen (DE); Stefan Kreusch, Golmsdorf (DE); Helga Endmann, Jena (DE); Michael Händel, Jena (DE); Günther Sammler, Jena (DE); Edith Zimmermann, Graitschen (DE)

(73) Assignee: SCIENOVA GmbH, Jena (DE)

( * ) Notice: Subject to any disclaimer, the term of this patent is extended or adjusted under 35 U.S.C. 154(b) by 1083 days.

(21) Appl. No.: 12/450,044

(22) PCT Filed: Mar. 7, 2008

(86) PCT No.: PCT/DE2008/000412
§ 371 (c)(1),
(2), (4) Date: Dec. 10, 2009

(87) PCT Pub. No.: WO2008/106960
PCT Pub. Date: Sep. 12, 2008

(65) Prior Publication Data
US 2010/0136596 A1 Jun. 3, 2010

(30) Foreign Application Priority Data
Mar. 8, 2007 (DE) .................. 10 2007 011 866

(51) Int. Cl.
| | |
|---|---|
| B01D 69/06 | (2006.01) |
| B01D 69/10 | (2006.01) |
| B01D 61/28 | (2006.01) |
| B01D 63/08 | (2006.01) |
| B01L 3/00 | (2006.01) |
| G01N 1/34 | (2006.01) |

(52) U.S. Cl.
USPC ............. 422/513; 422/50; 422/501; 422/503; 422/547; 422/549; 422/550; 422/552; 210/644; 210/295; 210/321.72; 210/321.75; 210/645; 210/646; 210/650; 435/283.1; 435/288.4; 436/174; 436/177

(58) Field of Classification Search
None
See application file for complete search history.

(56) References Cited

U.S. PATENT DOCUMENTS

| | | | | |
|---|---|---|---|---|
| 3,326,380 A | * | 6/1967 | Fechner et al. | ............... 210/253 |
| 3,746,175 A | | 7/1973 | Markley | |

(Continued)

FOREIGN PATENT DOCUMENTS

| | | |
|---|---|---|
| AU | 1460170 | 11/1971 |
| DE | 101 60 975 | 6/2003 |

(Continued)

OTHER PUBLICATIONS

2006 "Multidimensional proteomics of human serum using parallel chromatography of native constituents and microplate technology" Anton Horn et al. Proteomics vol. 6 pp. 559-570.

(Continued)

*Primary Examiner* — Jill Warden
*Assistant Examiner* — Timothy G Kingan
(74) *Attorney, Agent, or Firm* — Jordan and Hamburg LLP

(57) ABSTRACT

A device is provided by means of which biomolecules in samples in a volume range from <1 μl to 500 μl can be received, treated and stored in a quick, reproducible and loss-free manner as easily, effortlessly and practically as possible, and without any risk of damaging the device. The device includes sample vessels that are configured, in terms of size and shape, as dimensionally and positionally stable capillaries that are open at both ends, the longitudinal walls of which are completely or partially made of a semi-permeable membrane.

44 Claims, 9 Drawing Sheets

(56) References Cited

U.S. PATENT DOCUMENTS

| | | | |
|---|---|---|---|
| 3,827,563 | A * | 8/1974 | Boe et al. .................. 210/321.75 |
| 4,244,820 | A * | 1/1981 | Hauk et al. ...................... 210/194 |
| 4,931,160 | A * | 6/1990 | Giuffrida ...................... 204/632 |
| 5,503,741 | A | 4/1996 | Clark |
| 5,922,615 | A | 7/1999 | Nowakowski et al. |
| 6,187,190 | B1 | 2/2001 | Smith et al. |
| 6,297,060 | B1 | 10/2001 | Nowakowski et al. |
| 6,458,275 | B1 | 10/2002 | Shukla et al. |
| 6,494,614 | B1 * | 12/2002 | Bennett et al. ................ 366/336 |
| 6,998,047 | B1 | 2/2006 | Kopaciewicz et al. |
| 7,156,996 | B2 | 1/2007 | Watzele et al. |
| 7,166,458 | B2 * | 1/2007 | Ballerstadt et al. ........ 435/287.1 |
| 7,468,281 | B2 * | 12/2008 | Kallury et al. ................ 436/178 |
| 7,820,024 | B2 * | 10/2010 | Freydina ...................... 204/632 |
| 2003/0027216 | A1 | 2/2003 | Kiernan et al. |
| 2003/0167031 | A1 | 9/2003 | Odland |
| 2004/0084370 | A1 * | 5/2004 | Singh et al. .................... 210/645 |
| 2004/0195163 | A1 | 10/2004 | Watzele et al. |
| 2005/0019774 | A1 * | 1/2005 | Horn et al. ........................ 435/6 |
| 2005/0133425 | A1 | 6/2005 | Pitt et al. |
| 2005/0148066 | A1 | 7/2005 | O'Keefe et al. |
| 2005/0186118 | A1 | 8/2005 | Bishop et al. |
| 2006/0198765 | A1 | 9/2006 | Gjerde et al. |
| 2008/0093298 | A1 * | 4/2008 | Browning et al. ............ 210/646 |
| 2008/0197066 | A1 * | 8/2008 | Connors .................. 210/321.75 |

FOREIGN PATENT DOCUMENTS

| | | |
|---|---|---|
| DE | 2003 05 570 | 6/2004 |
| EP | 1 139 087 | 10/2001 |
| WO | WO-95/02182 | 1/1995 |
| WO | WO-98/37949 | 9/1998 |
| WO | WO-02/16652 | 2/2002 |
| WO | WO-02/082051 | 10/2002 |
| WO | WO-02/088672 | 11/2002 |
| WO | WO-03/083044 | 10/2003 |
| WO | WO-2004/032735 | 4/2004 |
| WO | WO-2004/101151 | 11/2004 |
| WO | WO-2005/070141 | 8/2005 |
| WO | WO-2005/103718 | 11/2005 |
| WO | WO-2006/055756 | 5/2006 |

OTHER PUBLICATIONS

2006 "Robust protein quantitation in chromatographic fractions using MALDI-MS of tryptic peptides" Renate Bublitz et al. Proteomics vol. 6 pp. 3909-3917.

1983 Medical Biochemistry, publishing company "Volk and Wissen" S.M. Rappoport Medical Biochemistry pp. 39-40.

Kirk-Othmer; "Hollow-Fiber Membranes"; Encyclopedia of Chemical Technology, 4th Edition, vol. 13, John Wiley & Sons, 1995, pp. 312-337.

* cited by examiner

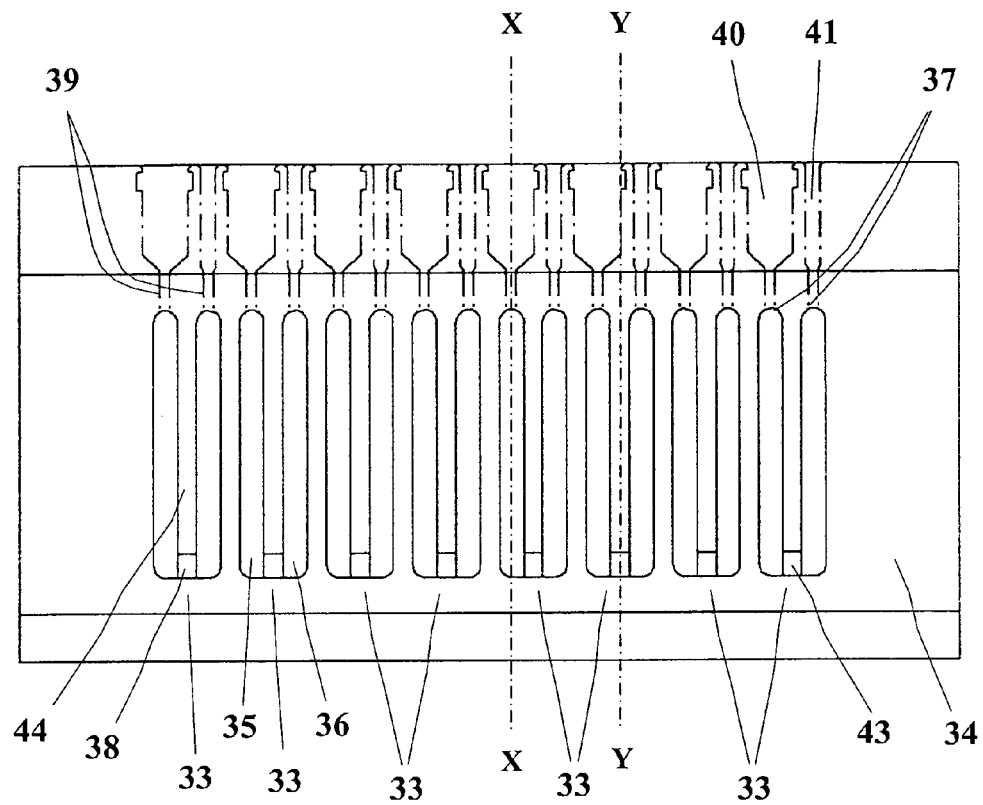
Fig. 4a
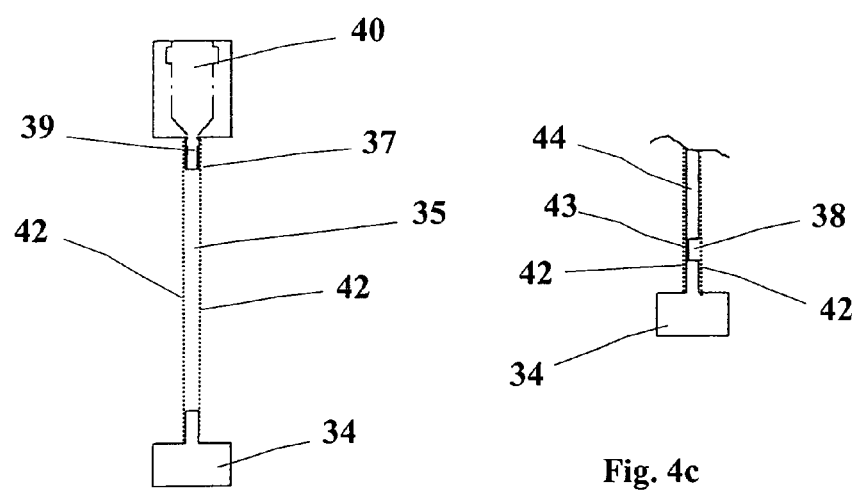
Fig. 4b
(Section X-X)
Fig. 4c
(Section Y-Y)

(Section X-X)

DEVICE FOR RECEIVING, TREATING, AND STORING SMALL VOLUME SAMPLES

BACKGROUND OF THE INVENTION

The present application relates to a device that allows for handling, storage, reception, and treatments of samples in as universal manner as possible, i.e., for the reception, for different treatments, and whereby the samples are handled in μl volumes.

Essential components of biological samples, biomolecules, analytes, and essential analytes are terms that are used within this invention as synonyms, particularly for such components to in the samples to be examined that are in the focus of the examiner's or user's interest and are contained together with the matrix. These are, for example, metabolites, nucleic acids, peptides, proteins, particles, cells, viruses, microorganisms, spores, markers, enzyme substrates or products, and others as a whole or parts thereof and/or complexes from them. Within this application, the term matrix stands for such components of a sample that are not in the focus of interest and often disturb the analysis processes, particularly the solvent and other accompanying substances, for example, salts, detergents, buffers, metal ions, antibiotics, and others.

The essential components of a sample usually differ from the matrix components in their size or molecular size.

In the course of preparative and analytical procedures, biological samples must be variously treated with respect to their essential components.

Such treatments include the addition of auxiliary reagents, such as urea or guanidine for denaturation, mercaptoethanol or dithiothreitol for reduction, iodoacetamide for modification, enzymes and their cofactors for the selective elimination of modifications or the selective digestion of essential analytes, substrates for proof of enzymatic activities, inhibitors for the suppression of undesired enzymatic reactions, capture reagents for binding undesirable substances, among others.

Frequently, it is necessary to transfer the essential components of biological samples into another medium, another matrix (see above), to ensure the compatibility in subsequent cleaning processes or for analytical procedures. As often only small quantities of possibly very precious samples are available and several analytical processes may be used for one sample it is recommended to transfer only very few partial quantities of the sample into the corresponding medium that is compatible with the relevant analysis. For mass spectrometry analyses a desalting is additionally required, i.e. a very drastic reduction of salt and detergent concentration in the matrix resulting in the receipt of low-molecular essential components in the range from 1000 to 3000 Da.

Although mass spectrometry procedures can be carried out with very small volumes (1-5 μl) they require relatively high analyte concentrations. To reach the sensitivity range it is often necessary to strongly concentrate the essential components of the samples in a preanalytical process. However when doing this, the concentrations of disturbing accompanying substances must not be increased in the same extent.

Analytical screening procedures and proteomics-based technologies cope with very large numbers of samples of the same type with each of said samples is to be submitted to a treatment or several identical treatments, such as medium changes, desalting or concentration procedures.

Normally, the medium change, which can also include a desalting process, is performed by three alternatively usable methods: gel chromatography, reverse-phase chromatography, and dialysis.

The gel chromatography is based on the chromatographic separation of matrix components in the dependency of the molecular weight. This process requires clean chromatographic conditions and at present relatively large sample volumes. The sample components after the medium change are always obtained in larger volumes than the source material and nowadays they are mostly in the ml-range. So far, the experts do not know a solution for a parallelization, i.e. the simultaneous handling of a plurality of samples of the same kind. A miniaturization would be imaginable but it requires sample-volume-dependent minimum separation lengths of the mini columns and thus also the volumes of the desalted samples that do not fall under a minimum value. In WO 9502182, for example, such a procedure is described in miniaturized scale for the prefractionation for capillary electrophoresis procedures.

Compared with this, parallelized analytical chromatographic separations to the nanofluidic scale are possible (e.g. WO 2004101151). However, this method cannot be used for a preparative application during sample pretreatment because the sample quantities fall below the sensitivity range of, for example, mass spectrometry procedures, and the sample components after chromatography are always obtained in larger volumes, i.e. are additionally diluted compared to the source sample.

By means of reverse-phase chromatography preferably hydrophobic sample components are bound to a solid hydrophobic phase. Afterwards, these supporting materials are washed, and during this procedure a potential loss of essential, particularly hydrophobic analytes, is possible, and then they are eluted in the desired salt-free medium. Here, concentration steps will be feasible, if advantageous adsorption and elution volumes are selected. Microprocedures have been developed for sample and elution volumes in the μl range in ZipTips of the company Millipore (WO 9837949) or in PerfectPure tips (company Eppendorf). A parallelization of these microprocedures is difficult to carry out or cannot be carried out at all due to the running behavior of the microcolumns, membranes or monolithic structures integrated into the pipette tips that is to be controlled by the analyzer.

Parallelizable spin-down systems that are arranged in arrays of hydrophobic membranes exist. Although a centrifuge must be used, these methods approximately correspond to a feasible parallelized handling (U.S. Pat. No. 6,998,047). However, these systems require considerably larger volumes than zip tips.

The solid phase extraction is mostly a special kind of reverse-phase chromatography and can also be performed in a highly miniaturized scale (EP 1139087). US 2006198765 describes a solution that offers a 96-fold parallelized solid phase extraction or optionally also affinity chromatography for smallest volumes. In WO 02082051 parallelized affinity matrices are used for the pretreatment of samples for mass spectroscopy, too. This principle is applied in numerous other patent specifications.

Reverse-phase chromatography, solid phase extraction and affinity chromatography are based on the principle that the one or more analytes wash out of the accompanying substances and also possibly concentrated by this process, if required. But in said processes these methods always select special analytes in dependency of the characteristics of the analytes and the characteristics of the solid phase.

In the dialysis procedure described herein the accompanying substances and the solvent are removed without considerably influencing the composition of the essential analytes of the sample.

Dialysis procedures and the relevant arrangements are nowadays available for the desired volume range from about 10 μl up to several liters. Usually, dialysis tubes, mini sacks or cartridges are used. Here, the medium change is realized via the diffusion of the low-molecular matrix components through a semi-permeable membrane whereas the essential sample components are restrained from diffusing.

Semi-permeable membranes in the sense of this invention are membranes that do not allow particles, cells or molecules of a defined maximum size (cut-off) to pass, i.e. permeate. This is achieved by the pores that are provided in the membrane and mostly have a narrow size range. The membranes can be frits with pores of several 100 μm, filtration membranes with pores in the μm and sub-μm ranges and molecular screen membranes with a molecular weight ranging from a few hundred DA to several 100 kDa.

The diffusion is a process that is initiated by the Brownian movement according to the Fick's laws of diffusion (1).

$$d_m = D \frac{q \times dc \times dt}{dl}, \quad (1)$$

wherein:
$d_m$=quantity of the diffusing substance
D=diffusion coefficient
q=diffusion cross-section or area
dc=concentration difference, and
dl=diffusion path
dt=diffusion time.

Additional factors that depend on the characteristics of the diffusing substance and of the membrane act at membranes.

For low-molecular matrix components the real diffusion times are directly proportional to the concentration gradient, the available area and inversely proportional to the diffusion path and normally amount to about 100 h for a diffusion path of 1.3 cm, about 1 h for 1.3 mm and about 0.3 sec for 13 μm (S. M. Rappoport, Medizinische Biochemie, Verl. Volk und Gesundheit, 1983, p. 39/40 [Medical Biochemistry, publishing company "Volk und Wissen"]).

Therefore, the diffusion will be useable for the efficient medium change, particularly for small volumes, if an appropriate geometry (large effective area, short diffusion paths) and suitable membranes (no interaction of the substances to be changed with the membrane) are used. Additionally, the concentration differences (dc in Formula 1) can be kept high by turbulences produced in the sample and/or the dialysis external liquid by appropriate mechanical systems and thus the diffusion through the membrane can be accelerated.

Bundles of hollow fibers with defined pores through which the sample liquid passes are also used for dialyses in the laboratory, and preferably for haemodialyses. In these methods, the same, mostly large-pored sample flows through a large number of bundled hollow fibers whereby the effective surface is considerably enlarged. Cartridges with semi-permeable membranes are also used for the medium change in the laboratory. Cartridges and hollow fibers have large total volumes due to the connection to pumps and require high pressures because the small cross-sections cause high flow resistances and the relatively thick walls act as long diffusion barriers. For this reason, it is difficult to integrate the two technical solutions in highly miniaturized or even parallelized systems.

In the laboratory, the dialysis can be performed in mini sacks or containers by simple pipette steps. Normally, the volumes of the samples are only changed insignificantly. If a suitable membrane type and pore size (molecular weight cut off) are selected, essential components of the biological samples will not be lost. However, a satisfying solution has not been developed so far for the simultaneous dialysis of a large number of small-volume samples that are of the same type but differ in the composition of essential analytes and matrix components. The "drop-dialysis", i.e. dialysis with comparably macropored filtration membranes swimming on the dialysis, is designed for the quick desalting of minimum volumes down to few μl but it cannot be parallelized and does not deliver a satisfying quantitative result with respect to the sample amount to be re-obtained and the essential components contained in it.

Singular dialysis systems down to a minimum volume of presently 10 μl exist (e.g. U.S. Pat. No. 5,503,741) but the surface-volume-ratio is not optimal at all and a parallelization is not planned. Moreover, special microdialysis units have been developed for even smaller volumes for the diffusion-based in vivo extraction of low-molecular solutes (WO 2004032735) but nor for the medium change of essential sample components, Here, a maximum surface-volume-ratio is achieved in the small interior chamber partly formed by a semi-permeable membrane but in said chamber a liquid is transported that shall absorb diffusible substances from the outside existing live tissue sample and thus transfer them to an analysis process. A parallelization is excluded here.

U.S. Pat. No. 6,458,275 shows a possible way to perform the parallelized equilibrium dialysis to investigate binding constants in microplate screens. In this method an own external liquid is provided for each sample and, due to the low volume ratio of the external liquid/sample it cannot be used principally for an efficient medium change or for desalting.

Parallelized dialyses are performed in different solutions. It is possible to use up to 12 samples and a volume of minimally 20 μl (Pierce: Microdialyzer System) or up to 96 samples and a minimum volume of approximately 24 μl (preferably in microplate screens) (e.g. US 2004195163, US 2005019774, US 2005148066, SpectrumLabs: Spectra/Por-Microdialyzer). Due to the unfavorable surface-volume ratios, the relatively small diffusion areas and the resulting relatively long diffusion paths, a complete medium change takes many hours in this method. As a result of the evaporation capacity at the large surface into the enclosed air chamber, evaporation losses occur during this time even if the sample vessels are covered, and essential components of the samples can, change. For example, proteins can denature. Moreover, it is difficult to parallelize the samples from the microplate-well-shaped sample vessels with fragile membranes and to retrieve them without many losses. A standardization of the dialysis conditions for all samples is not feasible because of the contingency of the formation of the effective diffusion path that is caused by volume tolerances, meniscus formation, and hardly controllable air bubble inclusions and air cushion development.

Sample plates for the application in dialysis systems are known (DE 101 60 975 A1) and can be used to dialyze a large number of microsamples in the μl range. These vessels, the upper ends of which are open and the lower ends, i.e. the front surfaces of the sample vessels, are closed by a filtration membrane used for the drop-dialysis, have been arranged in a screen suitable for the liquid handling method of microplate technology. However, a further reduction of the dialysis time and a minimization of the risk of damage, particularly of the semi-permeable membrane during the loading phase (pipette movement), would be desirable. Furthermore, the dialysis time depends on the filling level (diffusion path dl in Formula 1) and consequently on the sample volume as well as on the pipette precision.

To sum up, a completely satisfying feasible, rapid, reproducible procedure in which a medium change can be unselectively performed without losses for essential components of samples in the volume range from <1 µl to 500 µl in a short period of time has not been introduced so far. Dialysis processes that get into the lower range of the mentioned volumes are not quantitative and cannot be parallelized; the methods that can be parallelized require larger volumes and have considerable disadvantages in terms of handling, the likely precision and the required dialysis times.

Concentration processes are principally possible by means of precipitation reactions, ultra-centrifugation, ultra-filtration, lyophylization, incl. the special form by SpeedVac, and adsorption methods.

Precipitations by means of neutral salts, acids and organic solvents are efficient methods to increase the concentration for many analytes, such as proteins. However, these procedures are not suitable for low-molecular substances and peptides, are also not "unselective" for many other analytes because the analyte and matrix properties define the precipitation efficiency, and moreover, they mostly denature a large number of proteins. In addition to this, it is difficult to miniaturize and parallelize precipitation reactions and normally the means used for precipitation have to be removed from the sample before the actual analysis.

Ultra-centrifugation and ultra-filtration cannot be used for µl volumes, require flux supporting means, such as centrifuges or vacuum, and it is difficult to perform them in a parallelized manner.

The kit recommended in US 2005133425 includes single elements for ultra-filtration for the purpose of a molecular-weight-selective concentration and thus for a selective enrichment of selected analytes.

The lyophylization, also by means of SpeedVac, is actually a method that can be well parallelized and miniaturized but it has the disadvantage that the concentration of all disturbing accompanying substances is also increased due to the applied physical principle to of solvent evaporation. If this method is continued until the total solvent removal, i.e. the dryness, it is combined with the risk that the essential analytes, particularly the proteins or special peptides, are not/or only partially soluble again.

Adsorptions by means of specific capture bonds are elegant methods to highly enrich analytes on surfaces, but they imply also a preselection of bound analytes. These procedures can be easily parallelized. Their application is described, for example, for numerous SELDI-supports in different designs. In WO 2005103718 they are described for glycoproteins, in US 2003027216 for immunoreactive analytes, in WO 2005070141 for different analytes to be selected, and in all these procedures, an up to 96-fold parallelization is intended.

But also unspecific adsorption processes, such as the above described reversed-phase chromatography in zip tips, select special, here particularly hydrophobic, analytes. Miniaturized chromatographic adsorptive methods (US 2003027216, WO 2005070141) mostly require a flux support, such as centrifugal acceleration or vacuum.

Apart from the adsorptive systems that are described above and are only useable to a limited extent, such as zip tips with the known disadvantages, an arrangement and a feasible method that allow medium changes in combination with a considerable concentration of numerous parallel samples in the µl range and without the selection of a part of the sample components do not exist.

SUMMARY OF THE INVENTION

The object of the invention is to create a device by means of which biomolecules in samples in a volume range from <1 µl to 500 µl can be received, comprehensively treated and stored in a quick, reproducible and loss-free manner as easily, effortlessly and practically as possible and without any risk of damaging the device.

The samples shall be received and treated by utilizing the advantages of common liquid handling technology that is known for microplates, among others.

The device shall be equally useable for medium changes, concentration procedures and other sample treatments, storage included, without requiring modifications, re-pipetting or to refitting measures. Furthermore, preferably universally useable procedures without preference or selection of special analytes by possibly reactive surfaces shall be used.

The invention provides a device that includes at least one sample vessel for the universal receipt, treatment and storage of small-volume samples and is configured, in terms of size and shape, as a dimensionally and positionally stable capillary that is open on both sides and its longitudinal wall is completely or partially made of a generally known semi-permeable membrane.

The inventive capillary is a tubular sample vessel with a very small internal diameter. This capillary can be designed a straight tube or as a tube having one or more non-linear sections, that is, curved sections or angled sections between linear segments. For example, in an advantageous embodiment a U-shaped capillary is used and its openings on both sides are accessible from the same side of the device.

For its dimensional and positional stability it can be useful that the capillary has a form-fit connection, particularly at the areas of the capillary ends or face surfaces, with one or several supporting and thus dimension- and position-stabilizing elements, for example made of stainless steel or of a nonmetallic material, such as glass, ceramics or plastics. It is also possible that the sample vessel, which is manufactured as a capillary-shaped cavity, for example by means of molding, pressing, deformation or machining processes, is inserted—in terms of its size and shape—into a stabilizing body that can also include several partial bodies.

The semi-permeable membrane can be preferably connected to the stabilizing bodies by a permanent and sealing joint produced in principally known methods. Such processes are, for example, overmolding, IR welding, UV bonding or adhesion and have been used for producing permanent joints of very different polymer materials for a long time.

It is an advantage that the recommended capillaries can be arranged in a n×8×12 or n×8 or/and m×12 configuration, m and n each being an integer, wherein the samples are arranged in a microplate, thereby providing for a multiple sample treatment. Therefore, the application and compatibility of principally known and well-established methods of liquid to handling technology are ensured without complicated adjustments and re-fittings or separate methods of sample handling.

The recommended special sample vessel, particularly if it is provided in a microplate, allows the adoption of easily and practically manageable applications with extremely low losses despite very low sample volumes and a universal use for receiving, treating and storing samples, among others, also for increasing the concentration and for changing the medium. Thanks to the mentioned universal application possibilities, the otherwise required modifications, re-pipetting and refitting measures—which are combined with special efforts in sample handling, particularly for many thousands of samples in screening processes, and with the additional risk of sample losses and mix-ups—become superfluous. A geometry of the sample vessels for the parallelized dialysis of microvolumes has been found that does not only make short and thus effective diffusion paths possible, independently of the sample volume in the range of less than one millimeter, but its membrane arrangement also leads to a very efficient large diffusion area with respect to the volume.

Furthermore, the evaporation is minimized and a loss-free and easy-to-parallelize recovery of the dialyzed sample is made possible. In this way, the required diffusion time is drastically reduced and the high precision of this sample treatment step is ensured additionally. Moreover, further treatments are possible, if required, for example, the addition of modifying reagents the residuals of which can be removed without any extra efforts in a dialysis process after the reaction, or the digestion of protein analytes by means of specific proteases in the same sample vessel in which the medium change or a concentration was performed before, with a subsequent new concentration and desalting process.

Unlike the well-known solutions described above, the inventive semi-permeable membrane is not positioned at right angles to the loading direction—an arrangement that, according to general experience, cannot only rapidly cause damages when improperly used—but it is orientated as a complete or partial wall towards the axes or longitudinal direction of the capillary and thus the risk of damaging the membrane, particularly by the movement of the pipette, is quasi excluded.

The capillaries are preferentially designed so that the ratio of their length to the internal diameter is higher than 1:4. The largest extension of the cross-section of the capillaries should not be more than 5 mm. Moreover, the capillary openings can also be well handled and reliably closed, for example, by caps, plugs or adhesive films. Due to these characteristics, the risk of evaporation during the medium change performed by a dialysis process is reduced to a minimum and thus the high reproducible precision of the handling and the analysis of the samples is ensured.

The recommended capillary geometry with the proposed dimensions and the comparably large portion of the semi-permeable membrane allow the use of method-combined applications that can be well parallelized.

For example, if the device is submerged into an external liquid
a: the removal of dialysis-disturbing matrix components that are primarily contained in the sample,
b: the addition of auxiliary reagents, and
c: the removal of by-products after auxiliary reactions
can be realized by means of a dialysis via the external liquid without problems and a loss-free receipt of the essential analytes in small-volume samples. And the evaporation is minimized or excluded thanks to the comparatively small surfaces at the open capillary ends that can also be closed.

If the devices are stored in an evaporation-protected environment without any contacting external liquid, they can be used as parallelized reaction vessels for analytical auxiliary reactions or for storing and transporting samples, such as microplates or tubes.

If they are stored in a dry environment, possibly with controlled convection or vacuum, the evaporation of the solvent contained in the sample liquid through the large surface of the semi-permeable membrane can be utilized for increasing the concentration of essential analytes at high speed and advantageously without re-pipetting measures.

Any sequential combination of the described applications is also possible, even at different temperatures.

The capillarity of the sample vessels and the resulting cohesive forces of the liquid column as well as the non-selectivity of the semi-permeable membrane concerning the hydrophobic or hydrophilic character of the essential sample components allow the quasi complete recovery of said components.

Thanks to the explained possibilities and characteristics, the device can be universally and practically used for numerous parallelized processes with low efforts and a good precision and recovery of the essential components of a sample.

In the following, the embodiments of the invention are explained in detail in the following drawings.

BRIEF DESCRIPTION OF THE DRAWINGS

FIGS. 4a-4d depict formation of eight U-shaped capillary sample vessels in microplate screen size in a stable basic body
FIG. 4a is a front view;
FIG. 4b is a section along X-X according to FIG. 4a;
FIG. 4c is a section along Y-Y according to FIG. 4a;
FIG. 4d is a lateral view as a section of a stack of 12 stable basic bodies arranged one beside the other according to FIG. 4a with each of said bodies being provided with 8 U-shaped capillary sample vessels (cp. single representation of FIG. 4b);

FIG. 8a is a mass spectrum of sample 1, 2 pM protein, 10 mM Tris/HCl, pH 7.4 with 150 mM NaCl;
FIG. 8b is a mass spectrum of sample 2, 9.4 pM protein, ca. 53 mM Tris/HCl, pH 7.4 with 700 mM NaCl;
FIG. 8c is a mass spectrum of sample, 19 pM protein, 10 mM Tris/HCl, pH 7.4 with 100 mM NaCl.

DETAILED DESCRIPTION OF THE INVENTION

Example 1

Figure 1:
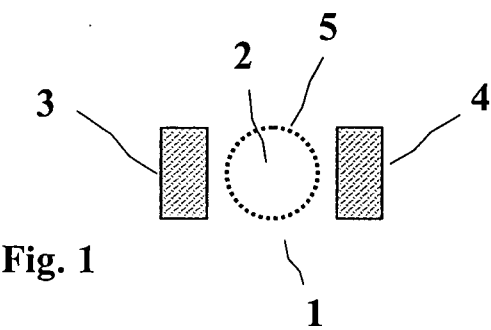
FIG. 1 is a top view of one capillary that is arranged between two stabilizing bodies and its wall has a round cross-section and completely consists of a semi-permeable membrane.

FIG. 1 shows a cross-section through a capillary sample vessel 1 with a circular cavity cross sectional area 2. For protection purposes, the capillary is arranged between two stabilizing bodies 3 and 4, which stabilize the capillary both dimensionally and positionally. The cylindrical cover surface (longitudinal wall) of the capillary sample vessel 1 completely consists of a semi-permeable membrane 5 (depicted in the sectional view of FIG. 1 as a circular dotted line).

Example 2

Figure 2:
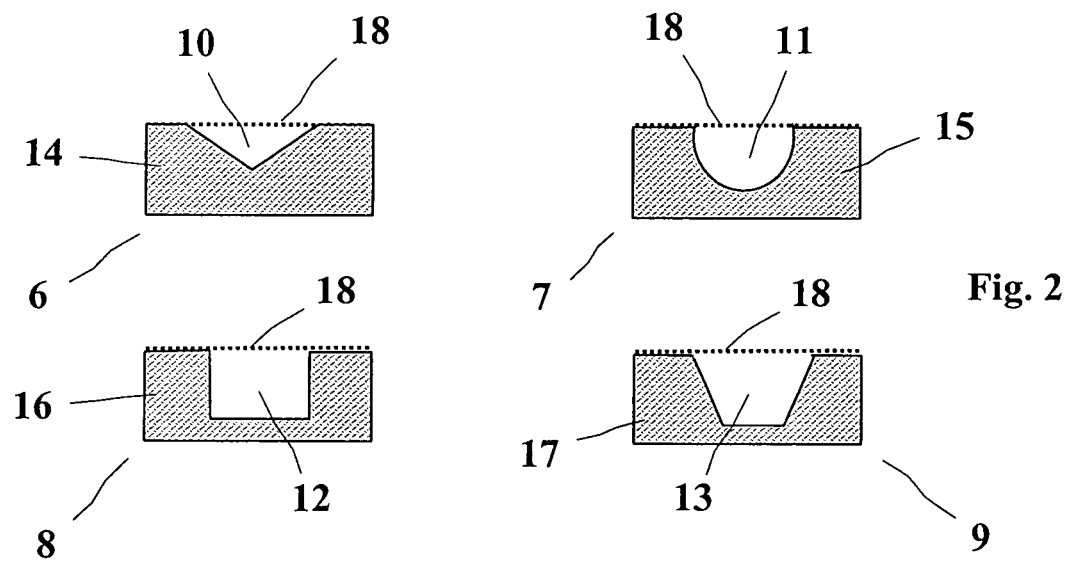
FIG. 2 is a top view of four capillaries with different cross-sections each of them formed as a cavity in a stable body and each of said cavities is closed by a semi-permeable membrane.

FIG. 2 also shows cross-sections through four capillary sample vessels 6, 7, 8, 9 with different cavity cross sectional areas 10, 11, 12, 13. In contrast to FIG. 1, in which the capillary is designed independently as a cylindrical cover surface by a semi-permeable membrane, i.e. independently of the adjacent stabilizing bodies 3, 4, each of the capillary sample vessels 6, 7, 8, 9 is a cavity formed in a stabilizing body 14, 15, 16, 17 that provides positional and dimensional stabilization for the capillary, with said cavity being produced, for example, by molding, pressing, deforming or machining processes. Each cavity in the stabilizing body 14, 15, 16, 17 is covered, for example, by an adhered or bonded semi-permeable membrane 18 (again represented as a dotted line) and thus the cavities of the capillary sample vessels 6, 7, 8, 9 are laterally closed. In this way, a capillary sample vessel 6 with a triangular cavity cross-sectional area 10 is formed in the stabilizing body 14, a capillary sample vessel 7 with a semicircular cavity cross-sectional area 11 is formed in the stabilizing body 15, a capillary sample vessel 8 with a rectangular cavity cross-sectional area 12 is formed in the stabilizing body 16, and a capillary sample vessel 9 with a trapezoidal cavity cross-sectional area 13 is formed in the stabilizing body 17.

Example 3

Figure 3:
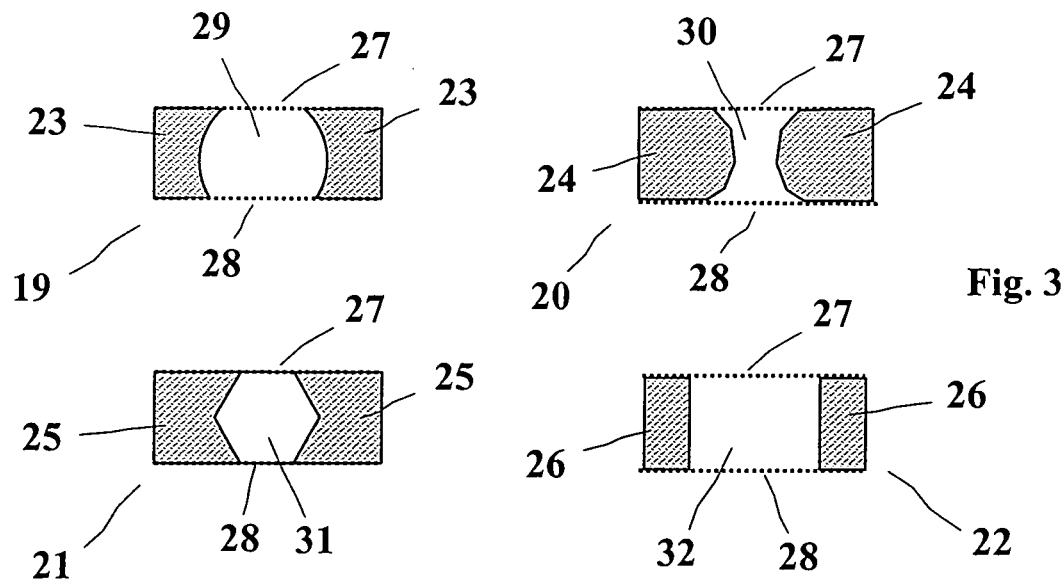
FIG. 3 are top views of four capillaries with different cross-sections each of them formed as an opening in a stable body with each of said openings being closed on both sides by a semi-permeable membrane.

Similar to FIG. 2, FIG. 3 also shows four cross-sections through capillary sample vessels 19, 20, 21, 22 each of them being realized in a stabilizing body 23, 24, 25, 26, which stabilize the capillary sample vessels both dimensionally and positionally. Unlike the capillaries in the embodiment in FIG. 2, the capillaries of this embodiment are not designed as cavities but each of them is formed by an opening through the body 23, 24, 25 and 26. The openings are covered by semi-permeable membranes 27, 28 (also represented as dotted lines here) on both sides. In this way, four capillary sample vessels 19, 20, 21, 22 are created and have differently shaped cavity cross-sectional areas 29, 30, 31, 32 shown in FIG. 3 as a curved cross section, a cross section with parallel walls, and as a plurality of cross sections formed of linear wall segments arranged at angles to each other.

Example 4

FIG. 4a illustrates a design of eight U-shaped capillary sample vessels 33 in a microplate grid in a n×8 array, wherein n=1, in a stabilizing body 34, which stabilize the capillary sample vessels both dimensionally and positionally. Each sample vessel 33 includes of two vertical capillary tubes 35, 36 that correspond to the cavity cross-sectional shape of sample vessel 22 in FIG. 3, are provided with upper open tube ends 37, and are connected to said U-shaped sample vessel at the bottom via a horizontal capillary tube 38 in form of sample vessel 8 (see FIG. 2). This capillary tube 38 preferentially contains a stabilizing connection bar 43, which restricts the lumen only partially, between a material lip 44 and the residual basic body 34.

At each sample vessel 33, the tube ends 37 of the capillary tubes 35, 36 are connected via a connection tube 39 with an opening 40 (capillary tube 35) for loading or removing the samples, not shown in the drawing for the sake of clarity, or with the ventilation opening 41 (capillary tube 36) for the sample filling or removal.

FIG. 4b shows a sectional view on the plane X-X indicated in FIG. 4a through the capillary tube 35 of a sample vessel 33 with an opening 40 for said sample loading or removal as well as a semi-permeable membrane 42 applied by bonding and thus completing the U-shaped sample vessel 33.

FIG. 4c shows a sectional view on the plane Y-Y indicated in FIG. 4a through the capillary tube 38 of a sample vessel 33 with the stabilizing connection bar 43, which restricts the lumen only partially, and the metal lip 44.

Figure 4D:
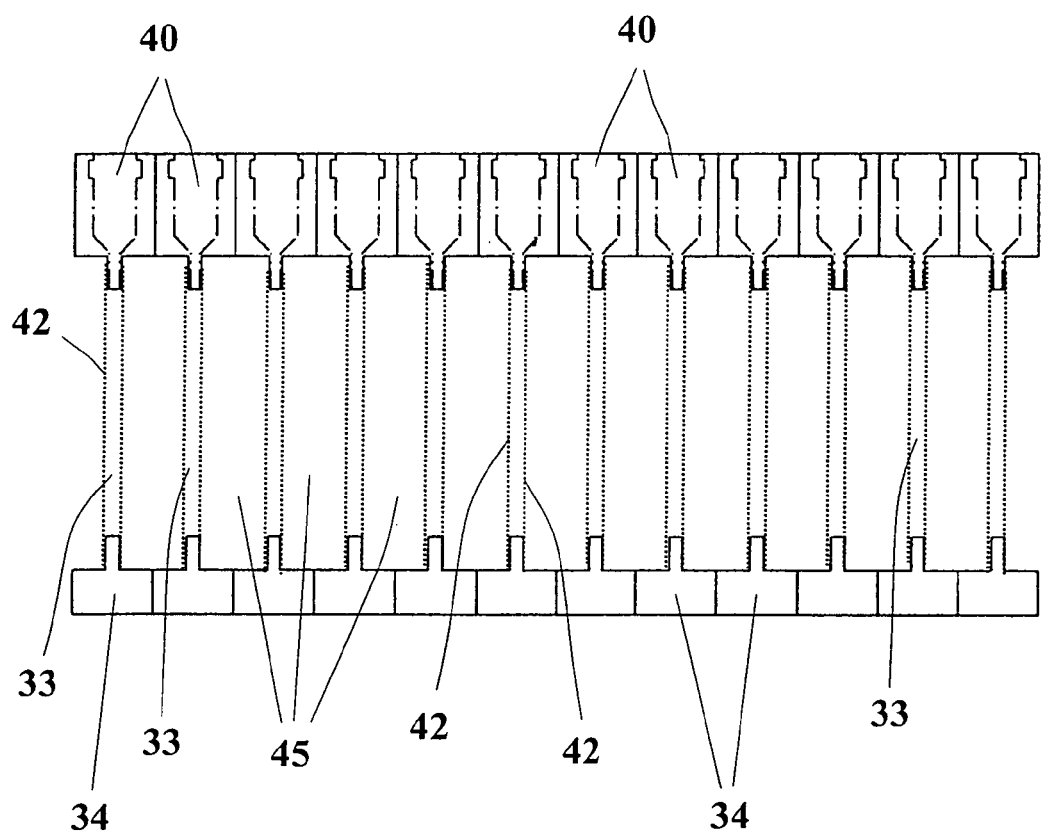

FIG. 4d shows a section in lateral view through a stack of twelve stabilizing bodies 34 that are arranged one beside the other according to FIGS. 4a-4d and each of them (as shown in FIG. 4a) is provided with eight U-shaped capillary sample vessels 33. The section X-X represented in FIG. 4b corresponds to the left sample vessel 33 in FIG. 4d. In FIG. 4d further eleven stabilizing bodies 34 are joined to the right (also realizable by means of only one stabilizing body for the whole block of the totally 96 existing sample vessels 33).

Thus, the U-shaped capillary sample vessels 33 are arranged here on several planes in a microplate grid array of n×8×12 wherein n=1 in accordance with known microplate screen dimensions. Between each of the twelve stabilizing bodies 34, which are placed one next to the other, comparatively large-lumen channels 4 are provided in which a dialysis external liquid (not shown) can exist or led through.

In the following, further embodiments are described to make the use of the inventive device clear.

Example 5

Medium Change Demonstrated at the Example of the Removal of the P-Nitrophenol Solution from a Solution in the Capillary Module In each of six of the eight U-shaped capillary sample vessels 33 according to FIG. 4a that have been developed by milling a stabilizing body 34 of polymethyl methacrylate (PMMA) and by adhesively bonding semi-permeable membranes 42 (Spektra/Por® 1, RC, MWCO 6-8 kDa, Spectrum-Labs), 200 µl of a solution containing 6 mM p-nitrophenol in 1 M diethanolamine/HCl, pH 9.8 (buffer A) are pipetted and a colorant-free buffer A is pipetted in two further capillary sample vessels 33. At room temperature, the module is put into a vessel containing 150 ml deionized water (external liquid). After 30 min the deionized water is replaced by fresh one. After always different periods of time the complete contents of all capillaries are soaked off by using a pipette, aliquots of them are diluted from 1 to 10 to 1 to 100 in buffer A in microplate wells and the absorbance is measured at 405 nm in a reader (Spectramax Plus384). The rest is pipetted back and further dialyzed.

Figure 5:
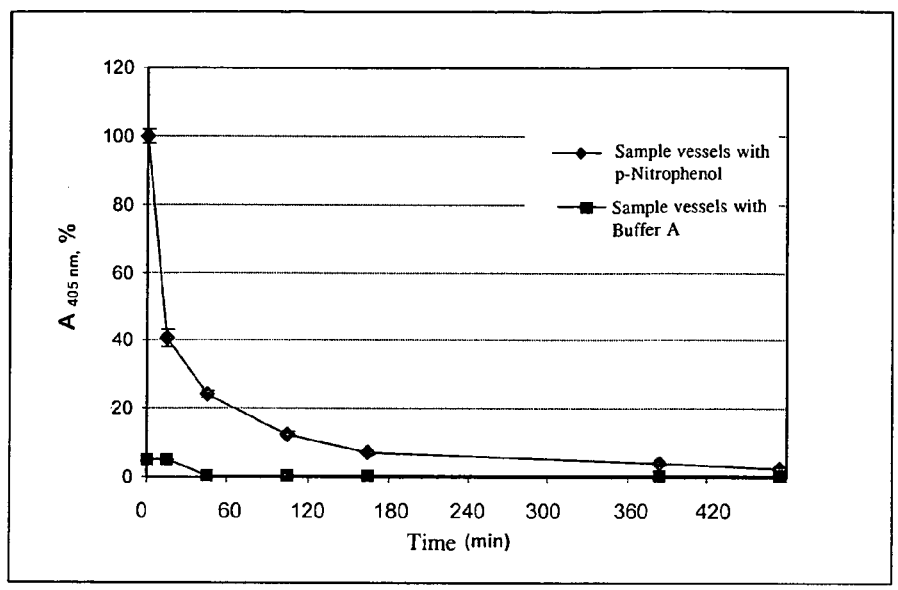
FIG. 5 is the time course of the reduction of the p-nitrophenol concentration in six simultaneously dialyzed samples by using U-shaped capillary sample vessels; mean values (points) and standard deviations (error bars) are indicated.

The diagram in FIG. 5 demonstrates that after approximately. 2 h only 12%, after approximately 3 h only about 7% of the initial colorant concentration are given. The low scattering of the single values clearly demonstrates the high reproducibility of this method.

The low colorant concentration in the capillaries filled with buffer A before the change of the external liquid is caused by the retrograde diffusion into the capillaries.

After the change (after 30 min) an absorbance cannot be proven any longer in the chambers filled with buffer A, i.e. the capillary sample vessels 33 completed by the adhesively bonded semi-permeable membrane are impermeable; a cross contamination does not happen.

Example 6

Removal of NaCl by the Capillary Module

In each of all eight U-shaped capillary sample vessels 33 (cp. FIG. 4a) 190 μl of a solution of 10 mM Tris/HCl, pH 7.4 (buffer B) with 150 mM NaCl are pipetted. At room temperature, the module is put into a vessel containing 150 ml buffer B (external liquid). After 30 min the external liquid is replaced by a new one. After always different periods of time the complete contents of all capillaries are soaked off by using a pipette. An osmometer (Knauer, semi-microosmometer) is used to measure the osmolarity of the solutions that is compared with calibration solutions then. Afterwards, the solutions are pipetted back and further dialyzed.

Figure 6:
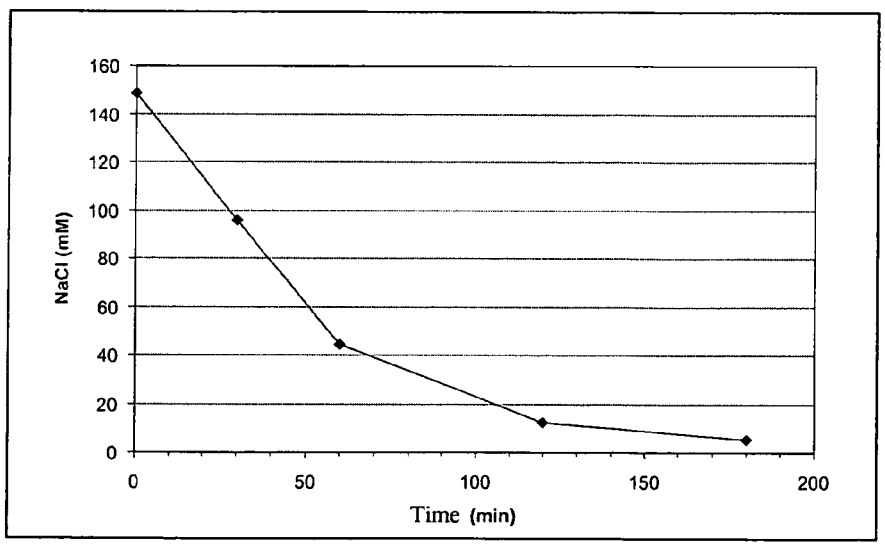
FIG. 6 is the time course of the reduction of the NaCl concentration in eight simultaneously dialyzed samples by using U-shaped capillary sample vessels; the mean values (points) are indicated.

In the diagram in FIG. 6 it can be seen that after 120 min or 180 min only about 8% or 4% of the initial NaCl concentration is given.

This method can be well reproduced because the variation coefficients of the corresponding 8-fold determinations are within the range of ≤1%.

Example 7

Evaporation of Water in the Capillary Module

200 μl deionized water are pipetted into each of the eight U-shaped capillary sample vessels 33 (cp. FIG. 4a). The module is fixed to a stand at normal room temperature and a van (diffuser, company Braun) placed at a distance of about 30 cm and oriented in the air flow is switched on at the lowest stage and without an additional heating. After different periods of time the module is weighed.

Figure 7:
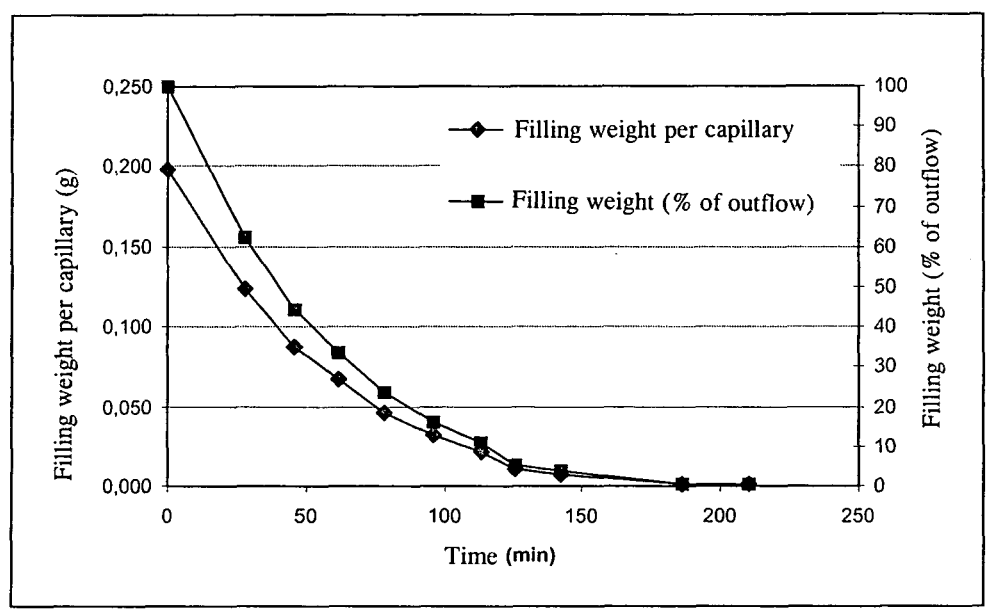
FIG. 7 is the time course of the volume reduction of eight samples simultaneously stored in U-shaped capillary sample vessels in the convection stream of a fan.

The diagram in FIG. 7 shows that after about 2 h about 5% and after 3 h only 0.6% of the initial liquid quantity still exist. This result would correspond to a concentration factor higher than 20 or approximately 160 if non-volatile analytes were present.

Example 8

Combined Sample Treatment

Concentration and Dialysis

190 μl of a solution with cow-IgG (Serva No. 22550, 0.3 mg/ml, 2.0 μM, in 10 mM Tris/HCl, pH 7.4, sample 1) are pipetted into each of the eight U-shaped capillary sample vessels 33 (cp. FIG. 4a). Like in example 7, the module is fixed to a stand and a van (diffuser, company Braun) placed at a distance of about 30 cm and orientated in the air flow is switched on at the lowest stage and without an additional heating. After the evaporation of the greater part of the liquid the residual volumes are combined in just one of the U-shaped capillary sample vessels 33 and the emptied capillary sample vessels 33 are sequentially rinsed with 100 μl 10 mM Tris/HCl, pH 7.4. The obtained rinsing liquid is added into the same capillary sample vessel 33 that contains said rest volume. The solution is again concentrated by means of the van (sample 2). Afterwards, it is dialyzed without any further re-pepetting in the same module during 2 h against 10 mM Tris/HCl, pH 7.4 with 100 mM NaCl d (sample 3).

Mass spectra of the samples 1 to 3 are registered by means of MALDI-MS (see A. Horn et al.: Proteomics, 6, 2006, 559).

Figure 8A:
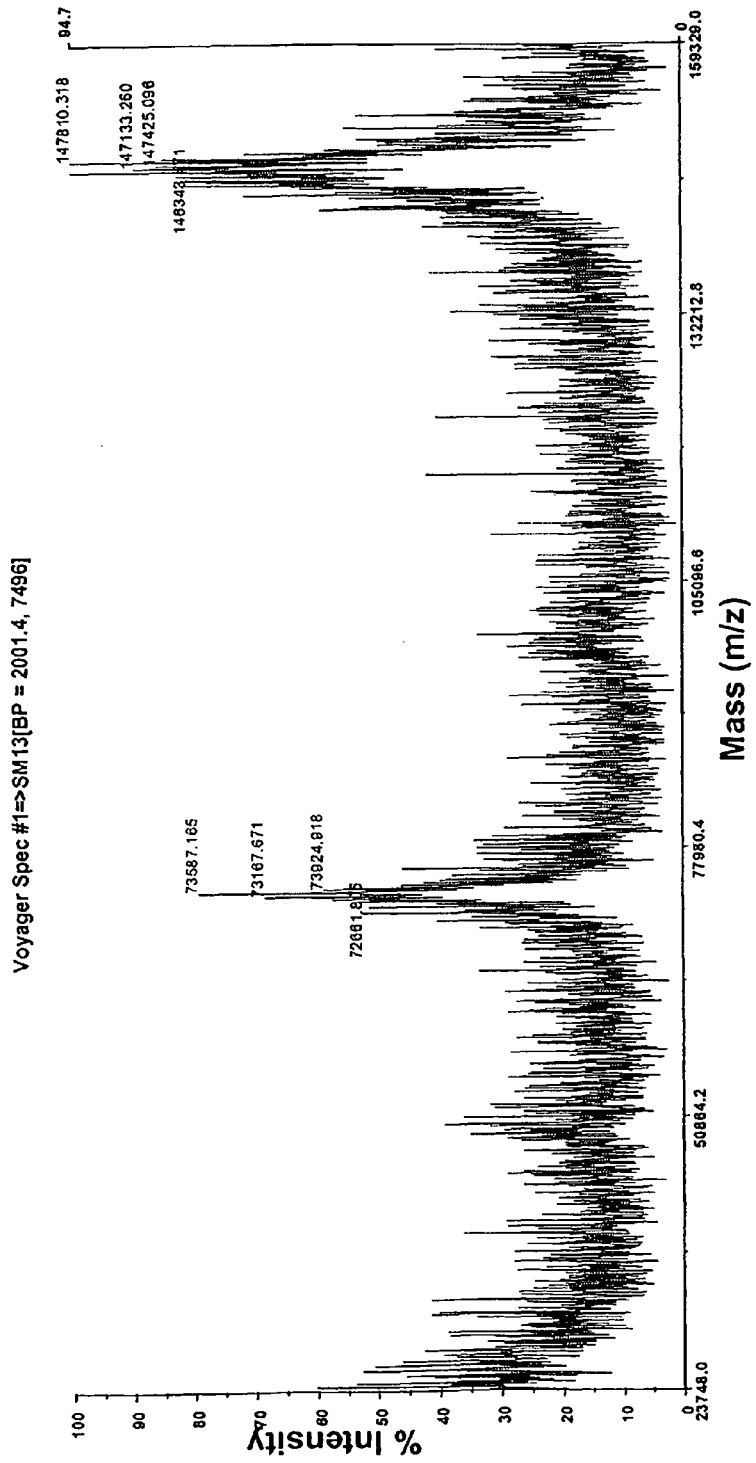
FIGS. 8a-8c depict mass spectra of the three samples according to embodiment 8.
Figure 8B:
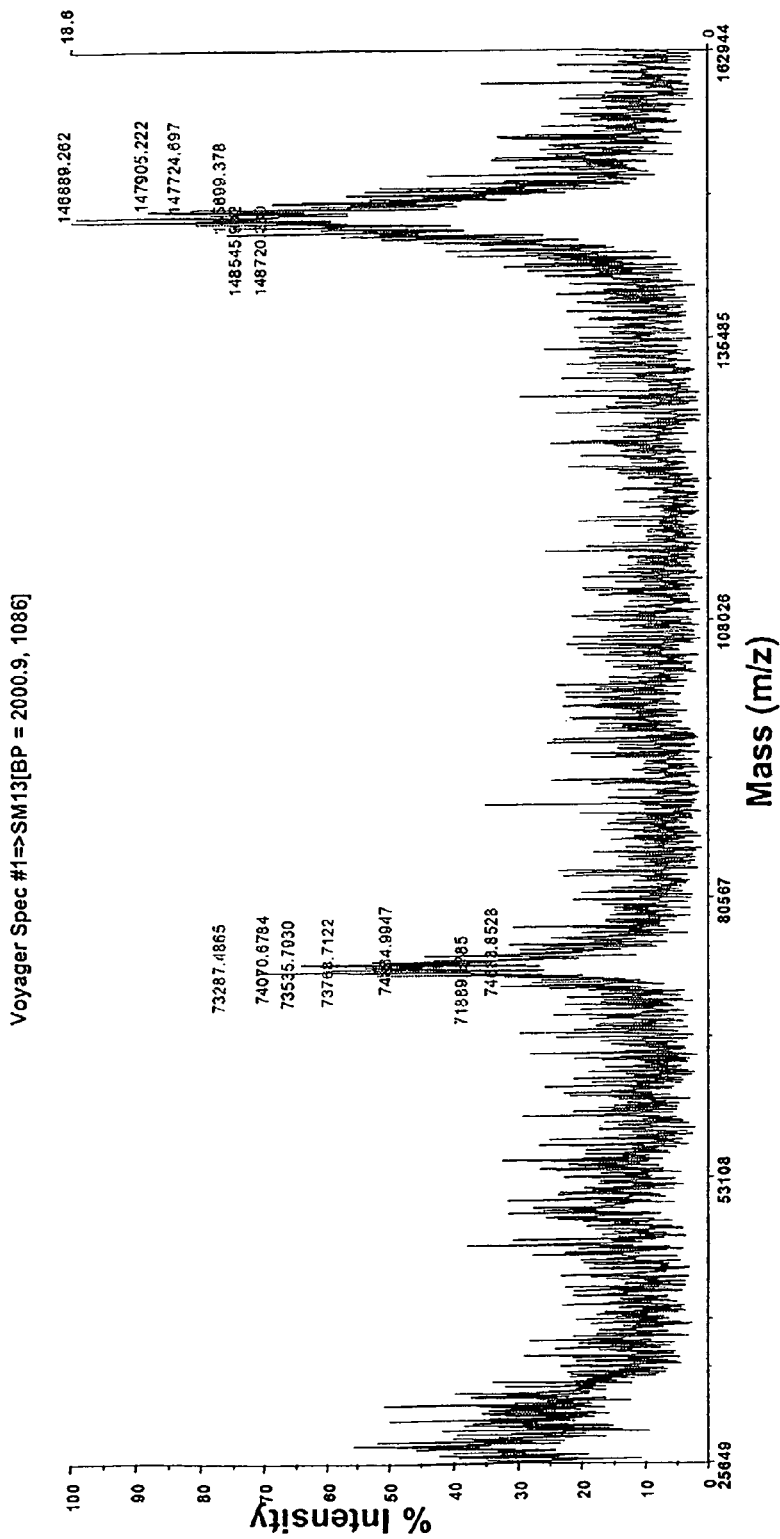
Figure 8C:
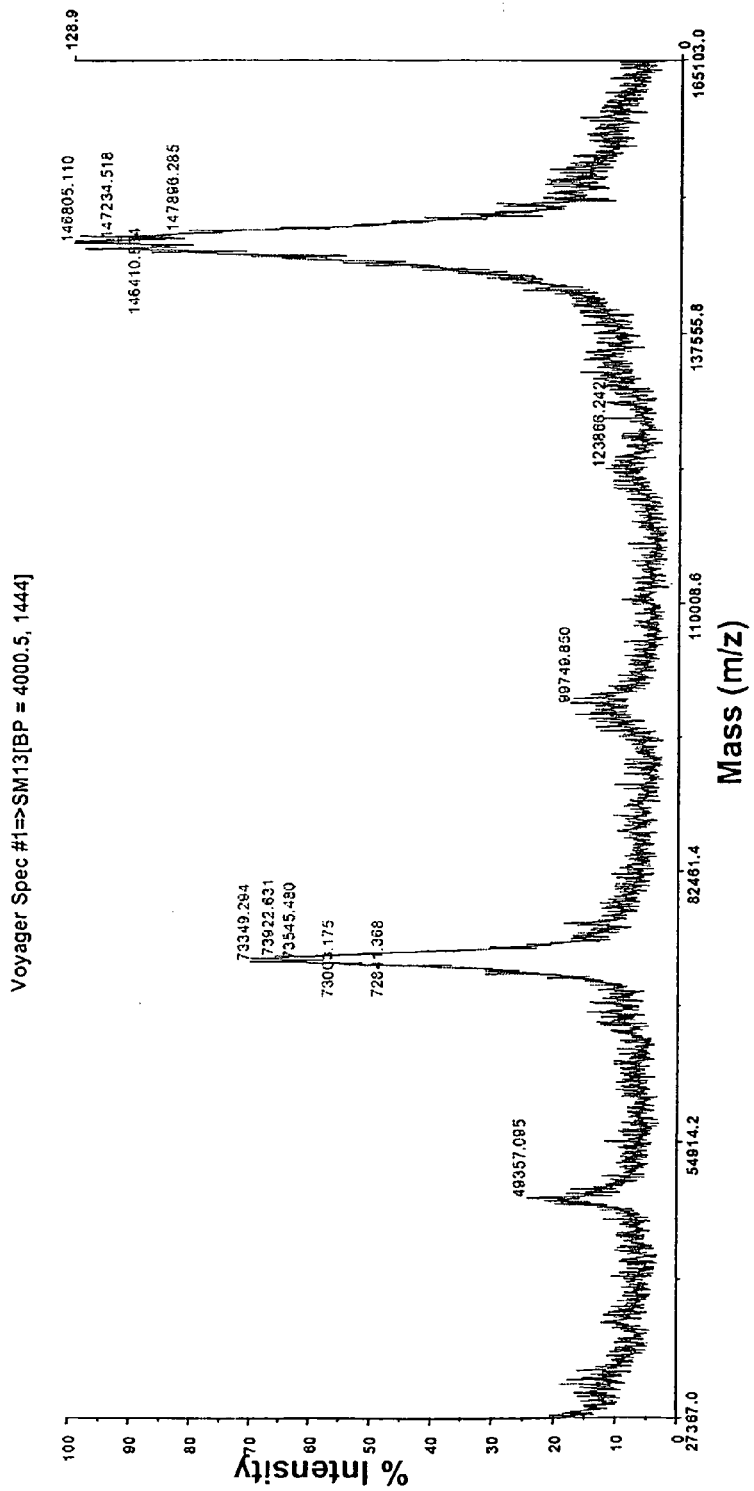

FIGS. 8a through 8c show the mass spectra of the samples 1 to 3.

The following table compares the sample volume, concentration factor and MALDI result of the three samples:

| Sample | Total volume (μl) | Concentration of IgG [μM] ca | Concentration of Tris/NaCl [mM] ca | Useful mass spectra Yes/No* | Concentration-factor (acc. to volume) |
|---|---|---|---|---|---|
| 1 | 1520 | 2.0 | 10/150 | No | 1.0 |
| 2 | 65 | 46.8 | 264/3510 | No | 23.4 |
| 3 | 80 | 38 | 10/100 | Yes | 19.0 |

*under the conditions specified in FIGS. 8a through 8c. Useful mass spectra are mass spectra that have a signal/noise ratio that is sufficiently high for the exact determination of the mean mass.

Example 9

Protein Modification, Dialysis and Digestion

After the addition of 20 μl 8 M Guanidin-HCL and denaturation in polycarbonate vessels at 90° C. for 20 min, 16 samples of human serum albumin (Sigma, 3 μM, always 60 μl in 20 mM ammonium-hydrocarbonate) are divided into two sets each consisting of 8 samples. One of these sample sets is parallel-modified as usual and digested in eight tubes (method A) or, as recommended as method B in said eight U-shaped capillary sample vessels 33 (see again FIG. 4a). The conventional method (method A) in tubes comprises the following operational steps that are performed one after the other: addition of DTT and iodoacetamide solution, with corresponding incubation, re-pipetting into dialysis vessels, 2 h-dialysis against 20 mM ammonium-hydrocarbonate, re-pipetting into new tubes, addition of trypsine and incubation. In the U-shaped capillary sample vessels 33 (method B) principally the same reactions take place but without the two re-pipetting procedures before and after the dialysis: Each of the peptide mixtures obtained in the corresponding eight sample vessels (tubes or U-shaped capillary sample vessels 33) after this treatment have been analyzed by MALDI-MS in four-fold determination per reaction vessel (Bublitz et al.: Proteomics 2006, 6, 3909). The results are compiled in the following table. It can be seen that the number of the peptides found, the achieved standardized height sums, which are a reliable quantitative mass-spectrometry measure, and the compositions of the found peptide mixtures are comparable for the application of the two methods.

| Parameter | Method A | Method B | Measured value |
|---|---|---|---|
| Refilling pipetting steps | 2 | 0 | number |
| Reaction vessels | 2 | 1 | piece |
| Number of found peptides | 37.1 ± 3.5 | 37.4 ± 5.4 | mean value ± SD (n = 32) |
| Standardized height sum of the found peptides* | 11.91 ± 2.94 | 9.15 ± 4.35 | mean value ± SD (n = 32) |
| Molecular weight of the found peptides (mean value of the mean values and of the SD) | 1521.02 498.31 | 1503.23 508.48 | kDa (n = 8) |
| Molecular weight of the found peptides (SD of the mean values and of the SD) | 56.34 42.33 | 45.90 58.42 | kDa (n = 8) |

*cp. Bublitz et al.: Proteomics 2006, 6, 3909,
SD: standard deviation

Example 10

Examination of Metabolites of Living Cells

Into each of the eight parallel U-shaped capillary sample vessels 33 (cp. FIG. 4a), 170 µl of, a suspension, containing one cell sediment part and four parts of physiological sodium to chloride solution (NaCl) are pipetted with freshly taken human erythrocytes washed in NaCl three times before. The module is put into a vessel with 10.0 ml NaCl with 10 mM glucose (external liquid) at room temperature. After always about 60 min, the external liquid is mixed, 100 µl are taken from it, and the module is again placed into the external liquid. In the samples taken the lactate concentration is measured according to Bergmeyer, H. U. in: Methods of Enzymatic Analysis, 3. Ed., Vol. VI, S. 582-588. Lactate in the external liquid can only be produced from glucose that enters into the capillaries by diffusion, be developed via the anaerobic glycolysis of the erythrocytes and be diffused back into the external liquid.

Figure 9:
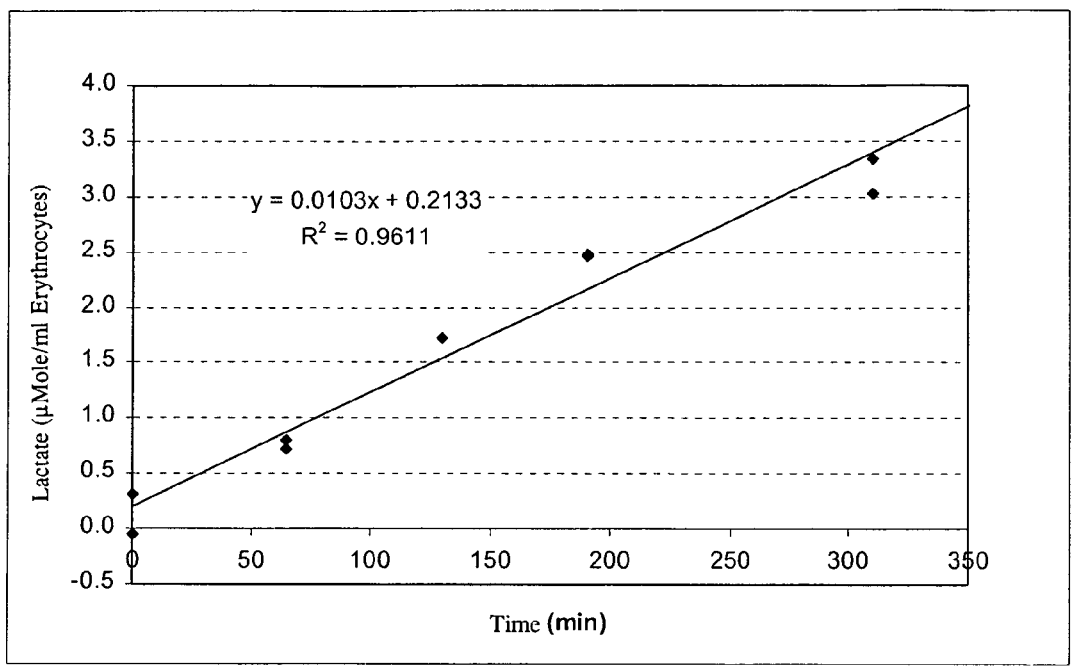
FIG. 9 depicts lactate production in human erythrocytes according to embodiment 10.

The diagram in FIG. 9 shows the lactate concentration in the external liquid for a period of 5 h. During this time, a linear concentration increase of this metabolite can be observed. The lactate produced under these conditions is 0.0103 µmole/(min×ml erythrocyte sediment) or ca. 0.7 µmole/(min×$10^{11}$ cells).

The advantage of this method is the fact that the packed cells can remain within the capillary without being disturbed, are maintained via diffusion and are liberated from metabolic end products such as lactate. Moreover, the selected membrane acts as a microbial barrier. The lactate determination is possible without time- and material consuming deproteinization because cells or macromolecules cannot pass through the membrane.

The invention claimed is:

1. A device for receiving, treating and storing small volume samples, comprising:
    a plurality of sample vessels each comprising a tube having a U-shaped configuration, each of the sample vessels sized and shaped as a capillary, each of the sample vessels being open on a first end and a second end, and having a first side wall comprising a semi-permeable membrane, a second side wall comprised of a second semi-permeable membrane, and at least one stabilizing body,
    the sample vessels being stabilized by the at least one stabilizing body, each of the sample vessels having an opening in the at least one stabilizing body, the opening being positioned between the first side wall comprised of the semi-permeable membrane and the second side wall comprised of the second semi-permeable membrane, the sample vessels being arranged as wells in a multiple well microplate, wherein the microplate is adapted for the handling of liquid samples.

2. The device according to claim 1, wherein the first and second semi-permeable membranes further comprise a material selected from the group of regenerated cellulose, cellulose ester, polyvinylidene difluoride, mixed cellulose esters, polyethersulphones, frits, glass fibers, filter papers, cellulose nitrate, nylon, polytetrafluoroethylene, other polyfluorocarbons, porous polyethylene, and polypropylene.

3. The device according to claim 1, wherein each of the sample vessels further comprises a third side wall, whereby two of the first side wall, the second side wall, and the third side wall are mutually parallel.

4. The device according to claim 1, wherein each of the sample vessels further comprises a third side wall, whereby two of the first side wall, the second side wall, and the third side wall are mutually non-parallel.

5. The device according to claim 1, wherein each of the sample vessels further comprises a round cross section.

6. The device according to claim 1, wherein each of the sample vessels further comprises a plurality of side walls arranged to provide the sample vessel with a polygonal cross section.

7. The device according to claim 1, wherein each of the sample vessels further comprises a ratio of length to inner diameter greater than 4.

8. The device according to claim 1, wherein maximum dimension of a cross section of each of the sample vessels is not greater than 5 mm.

9. The device according to claim 1, wherein each of the sample vessels has a capacity not exceeding 500 µl.

10. The device according to claim 1, wherein the sample vessels arranged in the microplate have identical capacities.

11. The device according to claim 1, wherein at least a portion of the sample vessels arranged in the microplate have, with respect to each other, non-identical capacities.

12. The device according to claim 1, wherein the number of sample vessels is 2 to 1536.

13. The device according to claim 1, wherein each of the sample vessels further comprises a cavity formed in the at least one stabilizing body.

14. The device according to claim 1, wherein the stabilizing body comprises a base plate which supports the sample vessels in a dimensionally and positionally stable arrangement and the base plate comprises the microplate for the handling of liquid samples.

15. The device according to claim 1, wherein the sample vessels are in a n×8×12, n×8, or m×12 arrangement, m and n each being an integer, wherein the sample vessels in the n×8×12 arrangement are arranged on a plurality of planes that are defined by the at least one stabilizing body.

16. The device according to claim 1, wherein the first side wall is further comprised of a non-permeable material and the semi-permeable membrane is permanently affixed to the non-permeable material.

17. The device according to claim 6 or 16, wherein each of the sample vessels is further comprised of side walls in addition to the first and second sidewalls, the side walls of each of the sample vessels being arranged in a polygonal cross section and whereby the first side wall comprising the semi-permeable membrane corresponds to a segment of the polygonal cross section.

18. The device according to claim 6 or 16, wherein each of the sample vessels is further comprised of side walls in addition to the first and second sidewalls, the side walls of each of the sample vessels being arranged in a polygonal cross section and the first and second side walls comprised of semi-permeable membranes correspond to at least two segments of the polygonal cross section.

19. The device according to claim 17 wherein the first side wall comprising the semi-permeable membrane is active in treatment of a sample.

20. The device according to claim 1, further comprising an adhering film provided over the open first end of each of the sample vessels whereby the adhering film provides a detachable closure for the sample vessels, which adhering film facilitates sample loading, sample removal and sample ventilation.

21. The device according to claim 1, further comprising detachable covers provided over the open first end of each of the sample vessels whereby the detachable covers facilitate sample loading, sample removal and sample ventilation.

22. The device according to claim 21 wherein the detachable covers are plugs.

23. The device according to claim 1, wherein the sample vessels are anchored, at a face surface of the sample vessels, to the at least one stabilizing body.

24. The device according to claim 1, further comprising a fitted connection between the sample vessels and the at least one stabilizing body, whereby the fitted connection provides the sample vessels with dimensional and positional stability.

25. The device according to claim 24, wherein the number of sample vessels is 2 to 1536.

26. The device according to claim 25, wherein all sample vessels are arranged on a plane that is the same as a plane of the at least one stabilizing body.

27. A device for receiving, treating and storing small volume samples, comprising:
- a plurality of sample vessels sized and shaped as a capillary, each of the sample vessels being open on a first end and a second end, and having a first side wall comprising a semi-permeable membrane, a second side wall comprised of a second semi-permeable membrane, and at least one stabilizing body,
- the sample vessels being stabilized by the at least one stabilizing body, each of the sample vessels having an opening in the at least one stabilizing body, the opening being positioned between the first side wall comprised of the semi-permeable membrane and the second side wall comprised of the second semi-permeable membrane, each of the sample vessels having an adhering film provided over the first open end of each of the sample vessels, whereby the adhering film provides a detachable closure for the sample vessels, the adhering film facilitating sample loading, sample removal and sample ventilation.

28. The device according to claim 27, wherein configuration of each of the sample vessels comprises a straight tube.

29. The device according to claim 27, wherein configuration of each of the sample vessels comprises a bent tube.

30. The device according to claim 29, wherein the each of the sample vessels further comprises an additional side wall having a curved shape.

31. The device according to claim 29, wherein the sample vessels are anchored, at a face surface of the sample vessels, to the at least one stabilizing body.

32. The device according to claim 29, further comprising a fitted connection between the sample vessels and the at least one stabilizing body, whereby the fitted connection provides the sample vessels with dimensional and positional stability.

33. The device according to claim 32, wherein the number of sample vessels is 2 to 1536.

34. The device according to claim 33, wherein all sample vessels are arranged on a plane that is the same as a plane of the at least one stabilizing body.

35. The device according to any one of claims 31, 32, 13, 33, 23, 24, 25 and 26, wherein the at least one stabilizing body is constructed of a material selected from metal, ceramics, plastics and glass.

36. The device according to any one of claims 31, 32, 13, 33, 34, 15, 23, 24, 25 and 26, wherein the at least one stabilizing body is produced by a process including casting, pressing, deforming or machining.

37. The device according to claim 27, wherein each of the sample vessels further comprises a tube having a U-shaped configuration.

38. The device according to claim 37, wherein the sample vessels are arranged as wells in a multiple well microplate, wherein the microplate is adapted for the handling of liquid samples.

39. The device according to claim 27, wherein the sample vessels are arranged as wells in a multiple well microplate, wherein the microplate is adapted for the handling of liquid samples.

40. The device according to claim 27, wherein the first and second semi-permeable membranes further comprise a material selected from the group of regenerated cellulose, cellulose ester, polyvinylidene difluoride, mixed cellulose esters, polyethersulphones, frits, glass fibers, filter papers, cellulose nitrate, nylon, polytetrafluoroethylene, other polyfluorocarbons, porous polyethylene, and polypropylene.

41. The device according to claim 27, wherein each of the sample vessels further comprises a round cross section.

42. The device according to claim 27, wherein each of the sample vessels has a capacity not exceeding 500 µl.

43. The device according to claim 27, wherein the number of sample vessels is 2 to 1536.

44. The device according to claim 27, wherein the sample vessels are in a n×8×12, n×8, or m×12 arrangement, m and n each being an integer, wherein the sample vessels in the n×8×12 arrangement are arranged on a plurality of planes that are defined by the at least one stabilizing body.

* * * * *